United States Patent [19]

Cullingford et al.

[11] 4,193,965
[45] Mar. 18, 1980

[54] CIRCUIT ASSEMBLY FOR EXHAUST EMISSION MONITORING

[75] Inventors: Christopher V. Cullingford, Inkberrow; Martin A. Read, Redditch, both of England

[73] Assignee: Lucas Industries Limited, Birmingham, England

[21] Appl. No.: 892,598

[22] Filed: Apr. 3, 1978

[30] Foreign Application Priority Data
Apr. 12, 1977 [GB] United Kingdom ............... 15101/77

[51] Int. Cl.² .................. G01N 27/04; G01N 27/26; H01C 7/00
[52] U.S. Cl. ............................. 422/95; 73/27 R; 204/195 S; 338/13; 422/98
[58] Field of Search ............... 23/232 E; 422/94, 95, 422/83, 98, 105; 73/27 R, 116; 204/1 S, 195 S; 338/13, 34, 22 SD; 60/276

[56] References Cited

U.S. PATENT DOCUMENTS

| | | | |
|---|---|---|---|
| 3,479,257 | 11/1969 | Shaver | 422/95 X |
| 3,603,954 | 9/1971 | Takuchi | 422/98 X |
| 3,911,386 | 10/1975 | Beaudoin et al. | 422/94 X |
| 3,936,794 | 2/1976 | Beaudoin et al. | 338/34 |
| 3,939,654 | 2/1976 | Creps | 60/276 |
| 4,001,758 | 1/1977 | Esper et al. | 422/105 X |
| 4,011,538 | 3/1977 | Froemel | 422/105 |
| 4,066,413 | 1/1978 | Segawa et al. | 422/98 |

*Primary Examiner*—Joseph Scovronek
*Attorney, Agent, or Firm*—Ladas, Parry, Von Gehr, Goldsmith & Deschamps

[57] ABSTRACT

A device for monitoring the composition of the exhaust emission of a combustion process includes a hollow elongated body open at one end thereof and an elongated substrate located in the body and defining adjacent the one end of the body an exhaust emission sensing element and a resistive heating element. The sensing element and the heating element are printed on opposite sides of one end of the substrate and are electrically connected to respective first conductive areas extending to the opposite end of the substrate. A carrier is mounted in the other end of the body and supports at least two terminal members which are electrically connected to respective second conductive areas provided on first and second elongated, flexible circuit elements which at their free ends project from the carrier and are folded inwardly so that said second conductive areas are presented to each other. The other end of the substrate is interposed between the folded portions of the first and second circuit elements so that said second conductive areas are aligned with said first conductive areas respectively, and a locating sleeve is engaged with said carrier so that said substrate and said folded portions of the first and second circuit elements extend through the sleeve. At least one clamping member is urged into a channel defined in the sleeve to trap the folded portions of said first and second circuit elements against the substrate. The first and second conductive areas are thereby urged into electrical contact with each other to electrically connect said terminal members to said sensing element and said resistive element respectively.

8 Claims, 5 Drawing Figures

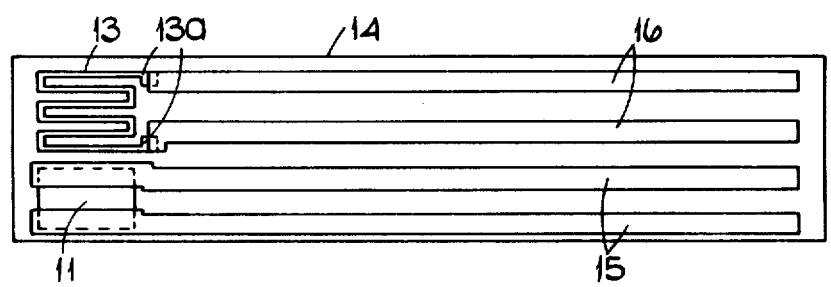
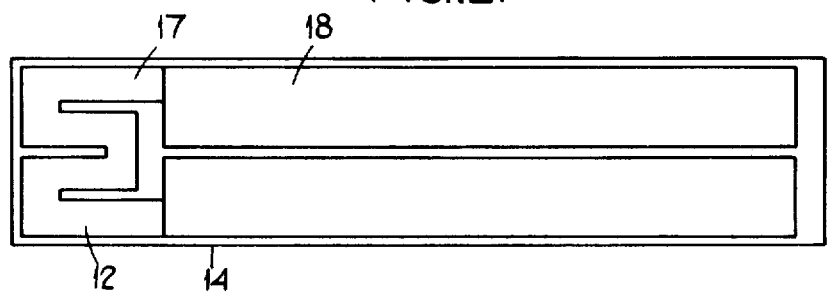
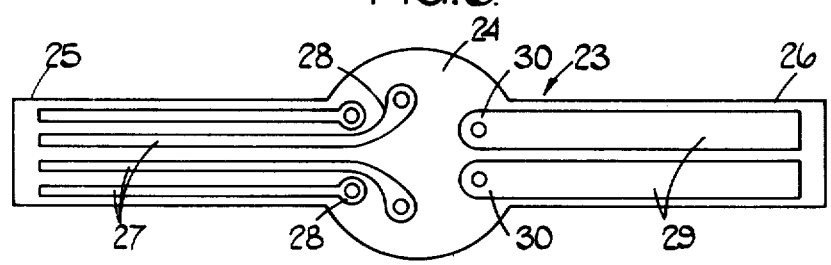

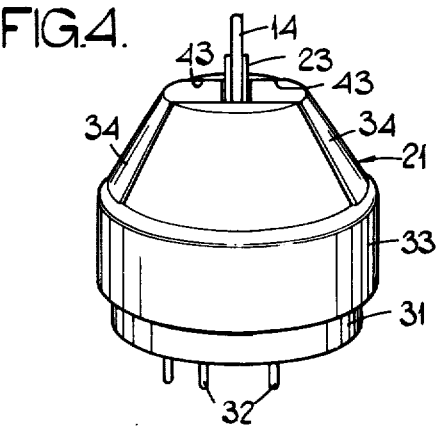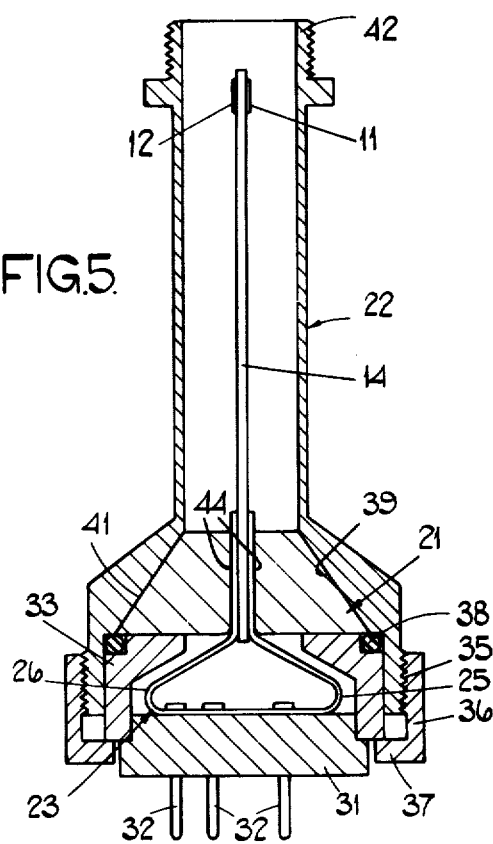

CIRCUIT ASSEMBLY FOR EXHAUST EMISSION MONITORING

This invention relates to a device for monitoring the composition of the exhaust emission of a combustion process and, in particular, of a road vehicle internal combustion engine.

A device, according to the invention, includes a hollow elongated body open at one end thereof, an elongated substrate located in the body and defining adjacent said one end of the body a sensing element and a resistive heating element, the sensing element and the heating element being printed on opposite sides respectively of the substrate adjacent one end of the substrate and being electrically connected to respective first conductive areas extending to the opposite end of the substrate, said sensing element being arranged so that, when raised to an elevated operating temperature by said heating element, its electrical characteristics vary with the concentration of oxidising or reducing constituents in the exhaust emission being sensed, first and second, elongated, flexible circuit elements each having an elongated second conductive area provided on one surface of the respective element and extending from one end of the element, a carrier mounted in the other end of the hollow body, said one end of each of said first and second circuit elements being secured to the carrier with the opposite ends of the elements projecting from the carrier and being folded inwardly so that said second conductive areas are presented to each other, at least two terminal members supported by the carrier and electrically connected to said second conductive areas respectively, the other end of the substrate being interposed between the folded portions of the first and second circuit elements so that said second conductive areas are aligned with said first conductive areas respectively, a locating sleeve engaged with said carrier so that said substrate and said folded portions of the first and second circuit elements extend through the sleeve, at least one clamping member movable in a channel defined in the sleeve and engaging at least one of the folded portions of said first and second circuit elements, and means urging said clamping member to trap said folded portions against the substrate whereby said first and second conductive areas are urged into electrical contact with each other to electrically connect said terminal members to said sensing element and said resistive element respectively.

Preferably, said circuit elements define respective portions of a single flexible circuit substrate.

Preferably, said channel in the sleeve is open at its opposite ends and receives a pair of said clamping members which are movable from said opposite ends respectively of the channel, under the action of said means, into engagement with said folded portions respectively to urge said folded portions against the first mentioned substrate.

Preferably, said means includes co-operating cam surfaces on the or each clamping member and said hollow body respectively.

Preferably, the first mentioned substrate is an elongated ceramic tile.

In the accompanying drawings, which illustrate one example of the invention:

FIG. 1 is a plan view of one surface of the ceramic tile of a device for monitoring the exhaust emission from a road vehicle internal combustion engine, FIG. 2 is a plan view of the opposite surface of the tile, FIG. 3 is a plan view to a reduced scale compared with FIGS. 1 and 2, of a flexible printed circuit substrate for providing the electrical connections to the tile, FIG. 4 is a perspective view of part of the device prior to assembly in the housing, and FIG. 5 is a sectional view of part of the assembled device.

Referring to the drawings, the device includes a metal oxide exhaust emission sensing element 11, a resistive heating element 12 and a temperature sensor 13, all of which are provided as printed layers on one end of an elongated insulating substrate 14. The sensing element 11 and the temperature sensor 13 are printed on one major surface of the substrate 14, (FIG. 1) whereas the heater 12 is printed on the opposite major surface of the substrate (FIG. 2) so as to be aligned with the element 11 and sensor 13.

The substrate 14 is in the form of a ceramic tile and preferably is an alumina-based tile having a low glass content in order to provide high mechanical strength, and provide a high electrical resistivity. To ensure an adequate resistivity a minimum alumina content of 99% is preferred.

The sensing element 11 is composed of a sintered mixture of titanium dioxide with 1 mol% of tantalum oxide and 1 atomic % of platinum. to produce this mixture, the components are heated together in air at 1100° C. for two hours, with the platinum conveniently being introduced into the starting material as platinous chloride. The sintered product is then ground to a powder which is classified by settling in water or any other suitable non-reactive fluid so as to remove particles of size in excess of 10 microns. The classified powder, which of course consists of particles of 10 microns and less in size, is then mixed with an organic carrier liquid, whereafter the resultant suspension is applied to the tile by conventional thick film screen printing techniques. Any conventional carrier liquid can be employed as the suspending phase and, for example, the carrier liquid supplied by Englehard Sales Limited as Medium 4/730 has been found to produce satisfactory results. It is, however, preferable to ensure that the suspension contains between 30 and 35 volume percent of the carrier liquid.

After the powder suspension has been printed on the tile 14, the resultant layer is dried at 120° C. for half to one hour and is then fired at 1200° C. to sinter the mixture into the required sensing element 11. The high temperature sintering operation is found to produce a strong bond between the element 11 and the tile 14 without the necessity for introducing a glass to improve the adhesion. Thus, using the mixture described above, it is found that the element 11 remains stable and strongly adhered to the tile 14 even at the high elevated temperatures (of the order of 900° C.) which the element experiences in use. The sintered element 11 is also found to be porous, which, in view of the resulting increase in surface area, provides an improved response time for the device and allows improved electrical connections to be made to the element.

The element 11 conveniently has a resistance value in air of 1 M ohms and preferably is shaped so as to have a low aspect ratio (length measured between conductive connectors: width measured parallel to connectors). Thus, in the preferred example shown, the element 11 is of rectangular configuration.

The sensor 13 is a platinum resistance thermometer which is printed on the tile 14 in a similar manner to that described for the element 11, although in this case the printing medium is a platinum ink in which the platinum particles preferably have a particle size no greater than 2 microns so as to enable the printing of a pattern with an accurate fine line width. The resultant layer is then dried at 120° C. and thereafter fired for 1 hour at 1200° C. to 1300° C. The firing operation is a longer and hotter process than is normal for platinum thick films, but this is desirable to promote ageing processes in the film so that the resistance of the film will be stable in service. The resultant sensor 13 is arranged to have a resistance value in air at 20° C. of the order of 10 ohms and preferably has a high aspect ratio, the latter being achieved in the preferred example by arranging the sensor 13 in the form of a narrow strip having the zig-zag configuration shown in FIG. 2 and provided with an enlarged terminal portion 13a at each end. After firing, the sensor 13 is conveniently protected by overprinting of a glass passivation layer.

When formation of the element 11 and sensor 13 is complete, first and second pairs of conductive areas 15, 16 are printed on the tile 14 to provide the necessary electrical connections to the element 11 and sensor 13 respectively. Each conductive area extends along the length of said one surface of the tile 14, with the area 16 overlapping the terminal portions 13a respectively of the rectangular element 11. Conveniently, the areas 15, 16 are produced by printing directly onto the tile 14 a gold-based, reactive bond, thick film ink of the kind supplied by E.M.C.A. as Type 3264, the printed layers being subsequently dried and then fired at 1000° C. The resistance of the resultant areas 15, 16 is sufficiently low to provide the required electrical connections to both the element 11 and the sensor 13.

Referring now to FIG. 2, the heating element 12 is of zig-zag configuration and extends over the whole width of said one end of the tile 14. The element 12 is produced by screen printing the required pattern on said opposite surface of the tile 14 using either the platinum ink composition supplied by Englehard Limited as No. 6082, or the platinum/gold composition supplied by E.M.C.A. as Type 180. The printing operation is also arranged to produce a pair of spaced connector strips 17 which extend along the length of the tile adjacent its opposite edges and which are joined to the ends respectively of the element 12. After printing, the ink layer is dried and fired either at 1200° C. in the case of the platinum/gold composition or at 1150° C. in the case of the platinum composition. Conductive areas 18 are then printed over the strips 17 respectively to provide the required electrical connections to the heating element 12, the conductive areas being produced from the unfluxed, pure gold printing composition supplied by E.M.C.A. as Type 213U. The printed layers are then fired at 800° C. to produce the required conductive areas 18, which conveniently have a resistance of about 150 m ohms. The heating element 12 is then preferably coated with a glass layer to improve its long term stability.

As shown in FIGS. 4 and 5, the tile 14 and its associated circuit elements form part of a circuit assembly 21 which, in the completed exhaust emission sensing device, is mounted in a heat resistant, hollow cylindrical body 22. The assembly 21 also includes an elongated, flexible, circuit substrate 23 which includes a generally circular central portion 24 and a pair of end portions 25, 26 which extend from diametrically opposite regions respectively of the portion 24 and are substantially the same width as the tile 14. Extending along one surface of the end portion 25 are four transversely spaced, elongated conductive areas 27 which correspond in shape and relative position to the conductive areas 15, 16 and which each continue onto the central portion 24 to define a respective enlarged terminal land 28. Similarly, the end portion 26 is provided with a pair of transversely spaced, further elongated conductive area 29 which extend along said one surface of the substrate onto the region 24 to define further terminal lands 30 and which correspond in shape and relative position to the conductive areas 18. The substrate 23 is formed of a polyimide which, as supplied, is coated over said one surface with a layer of copper bonded to the polyimide by a fluorinated ethyl propylene copolymer. To produce the conductive areas 27 to 30, the as-supplied substrate is etched through a mask to leave a copper pattern on said one surface of the substrate defining the shape of the required conductive areas, whereafter the copper layers are plated with a 5 micron thick layer of gold. The central portion 24 of the substrate 23 is mounted on one end surface of a generally circular carrier disc 31, with the other surface of the substrate remote from the conductive areas being presented to the carrier and with the end portions 25, 26 projecting from the carrier. Supported by the carrier 31 are a plurality of headed terminal pins 32 which extend through the carrier 31 and respective holes in the terminal lands 28,30 and which are secured by means of high temperature solder to their respective terminal lands. Thus the pins 32 provide electrical connections to the conductive areas 27,29 and in use, define the external terminals of the device.

The projecting end portions 25, 26 of the substrate 23 are folded inwardly so that the conductive areas 27,29 are presented to each other and so that the portions 25, 26 can pass through a locating sleeve 33 which is mounted at one end on the carrier 31. At its opposite end, the sleeve 33 defines a parallel-sided channel 43 which receives a pair of separate clamping members 34 which are of generally the same height as the channel and which are movable into the channel from opposite open ends respectively of the channel to define mutually presented parallel abutment surfaces 44. Extending through said other end of the sleeve 33 so as to be interposed between the folded end portions of the substrate 23 is the end of the tile 14 remote from the operating elements 11 to 13. The width of the channel 43 is generally equal to the width of the tile 14 and portions 25, 26 and hence the sleeve 33 serves to locate the tile 14 and portions 25, 26 against relative lateral movement. Moreover, the tile 14 is inserted between the folded portions 25, 26 by a sufficient distance to ensure that the conductive areas 27 are aligned with the conductive areas 15, 16 respectively over a substantial length of the areas 27, and a substantial length of each area 29 is aligned with its respective area 18.

As shown in FIG. 5, the assembly 21 comprising the sleeve 33, the carrier 31, the substrate 23 and the tile 14 is mounted in one end of the housing 22 with the region of the tile 14 projecting from the sleeve 33 extending towards, but terminating a short distance from, the other end 42 of the housing. At the other end 42, the housing is externally screw-threaded to facilitate mounting of the device in the exhaust system of the associated vehicle, while a further externally screw-threaded portion 35 is provided at said one end of the housing. Engaged with the portion 35 is an internally screw-threaded nut 36 having an inturned lip 37 which urges the assembly 21 into the housing 22 to trap an O-ring seal 38 between the sleeve 33 and the internal walls of the housing. Formed on the internal wall of the housing engaging the sleeve 33 is a cam surface 39 which is formed complementarily with further cam surfaces 41 defined by the members 34 and the associated portion of the sleeve 33. The arrangement of the surfaces 39, 41 is such that, when the nut 36 is screwed onto the portion 35, the members 34 are urged towards each other along the channel 43 so that the surfaces 44 clamp the folded portions 25, 26 non-resiliently against the tile 14. The conductive areas 27, 29 are thereby urged into contact with the associated areas on the tile 14 over substantially the entire height of the channel 43 so as to provide electrical connections between the terminal pins 32 and the sensing element 11, the heating element 12 and the temperature sensor 13.

When the device described above is used to monitor the composition of exhaust emission from an internal combustion engine, current is supplied by way of the terminal pins 32, and the conductive areas 29, 28 to the heating element 12 so as to heat the sensing element 11 to its required operating temperature, normally 900° C. At this temperature, the electrical conductivity of the element 11 varies in accordance with the amount of oxidising or reducing constituents in the exhaust emission and hence a measure of the emission composition can be obtained by connecting the terminal pins associated with the element 11 to a voltage source and then measuring the current flowing through the element 11. In order to obtain accurate sensing, however, it is necessary to ensure that the element 11 is maintained at a substantially constant temperature. This is readily achieved in the example described since the temmperature sensor 13 is positioned adjacent the element 11 and hence, in use, will be heated by the heating element 12 to substantially the same temperature as the element 11. Thus, by monitoring the resistance of the sensor 13, which is of course temperature dependent, the temperature of the element 11 can be closely followed and, where necessary, the current supplied to the heater be varied to retain the element 11 at its required operating temperature.

In use, it is found that the device described above enables the composition of the exhaust emission from a road vehicle internal combustion engine to be sensed accurately over extended periods despite the onerous temperature and environmental conditions to which the device is subject. Moreover, replacement of the component most suceptible to wear, the tile 14, can readily be achieved by simply unscrewing the nut 36 and removing the assembly 21 from the housing 22.

In an alternative embodiment (not shown), the substrate 23 is mounted on the carrier 31 so that the conductive areas 27,29 are presented to the carrier and the projecting end portions 25, 26 are folded inwardly and then bent back on each other so that the conductive areas 27,29 are still presented to the associated areas on the tile 14. Using this arrangement, it is preferred to produce the sleeve 33 and the clamping members 34 from an insulating material such as a ceramic.

As a further alternative, the flexible circuit substrate 23 can be replaced by two separate circuit elements, one element having the end portion 25, the conductive areas 27 and the terminal lands 28, and the other element having the end portion 26, the conductive areas 29 and the terminal lands 30. Moreover, by arranging that the channel 43 is closed at one end, a single clamping member 34 can be used instead of the pair of clamping members employed in the example shown. The single member 34 would then be urged by the cam surfaces 39,41 to trap the folded portions 26, 26 and the tile 14 against the closed end of the channel so as to provide the required electrical connection between the conductive areas 27,29 and the associated areas on the tile 14. Yet a further substrate alternative is to replace the ceramic tile 14 with an elongated metal plate having an insulating coating. In addition, although the exhaust emission sensing element disclosed is in the form of a metal oxide whose electrical conductivity varies in accordance with the composition of the emission, other types of sensing elements could be employed. Thus, for example, it would be possible to employ a metal oxide sensing element exhibiting a variable thermoelectric effect, and hence a variable voltage, in response to the exhaust emission composition. As a further alternative the exhaust emission could be sensed by means of an electrochemical cell having a reference electrode exposed to a controlled gaseous composition, for example oxygen, and a test electrode exposed to the exhaust emission. Such an electrochemical cell could conveniently be produced as a multi-layer thick film deposit on a substrate inert to the emission being sensed.

We claim:

1. A device for monitoring the composition of the exhaust emission of a combustion process including a hollow elongated body open at one end thereof, an elongated insulating substrate located in the body and defining adjacent said one end of the body a sensing element and a resistive heating element, the sensing element and the heating element being printed on opposite sides respectively of the substrate adjacent one end of the substrate and being electrically connected to respective first conductive areas extending to the opposite end of the substrate, said sensing element having electrical characteristics which vary with the concentration of oxidising or reducing constituents in the exhaust emission being sensed when the sensing element is raised to an elevated operating temperature by said heating element, first and second, elongated flexible circuit elements each having an elongated second conductive area provided on one surface of the respective element and extending from one end of the element, a carrier mounted in the other end of the hollow body, said one end of each of said first and second circuit elements being secured to the carrier with the opposite ends of the elements projecting from the carrier and being folded inwardly so that said second conductive areas are presented to each other, at least two terminal members supported by the carrier and electrically connected to said second conductive areas respectively, the other end of the substrate being interposed between the folded portions of the first and second circuit elements so that said second conductive areas are aligned with said first conductive areas respectively, a locating sleeve engaged with said carrier so that said substrate and said folded portions of the first and second circuit elements extend through the sleeve, at least one clamping member movable into a channel defined in the sleeve and engaging at least one of the folded portions of said first and second circuit elements, and means urging said clamping member to trap said folded portions against the substrate whereby said first and second conductive areas are urged into electrical contact with each other to electrically connect said terminal members so said sensing element and said resistive element respectively.

2. A device as claimed in claim 1, wherein said circuit elements define respective portions of a single flexible circuit substrate.

3. A device as claimed in claim 1, wherein said channel in the sleeve is open at its opposite ends and receives a pair of said clamping members which are movable from said opposite ends respectively of the channel, under the action of said means, into engagement with said folded portions respectively to urge said folded portions against the first mentioned substrate.

4. A device as claimed in claim 1, wherein said means includes co-operating cam surfaces on the, or on each clamping member and said hollow body respectively.

5. A device as claimed in claim 1, wherein the, or each, clamping member urges said first and second conductive areas into electrical contact with each other over substantially the full height of the channel.

6. A device as claimed in claim 1, wherein said sleeve serves to locate said substrate and said folded portions of the circuit elements against relative lateral movement.

7. A device as claimed in claim 1 wherein said first-mentioned substrate is an elongated ceramic tile.

8. A device as claimed in claim 1, wherein a temperature sensor is printed on the substrate adjacent the sensing element and on the same surface of the substrate as the sensing element.

* * * * *